United States Patent
Trolinder et al.

(10) Patent No.: US 7,122,722 B2
(45) Date of Patent: Oct. 17, 2006

(54) METHODS FOR PRODUCING TRANSGENIC COTTON PLANTS USING CHILLED APICAL SHOOT TIPS

(75) Inventors: Norma L. Trolinder, Quanah, TX (US); Linda K Koonce, Idalou, TX (US); Jane K. Dever, Lubbock, TX (US)

(73) Assignee: Cotton Incorporated, New York, NY (US)

( * ) Notice: Subject to any disclaimer, the term of this patent is extended or adjusted under 35 U.S.C. 154(b) by 139 days.

(21) Appl. No.: 10/409,055

(22) Filed: Apr. 9, 2003

(65) Prior Publication Data

US 2003/0208795 A1    Nov. 6, 2003

Related U.S. Application Data

(63) Continuation of application No. 09/252,477, filed on Feb. 18, 1999, now abandoned.

(60) Provisional application No. 60/075,261, filed on Feb. 19, 1998.

(51) Int. Cl.
- *A01H 5/00* (2006.01)
- *C12N 15/09* (2006.01)
- *C12N 15/82* (2006.01)
- *C12N 15/84* (2006.01)
- *A01H 1/00* (2006.01)
- *C12N 15/00* (2006.01)

(52) U.S. Cl. ............ 800/294; 800/314; 800/298; 435/252.2; 435/430; 435/430.1

(58) Field of Classification Search ............ 435/430, 435/430.1, 468, 419, 69.1, 252.3; 800/278, 800/298, 314, 294
See application file for complete search history.

(56) References Cited

U.S. PATENT DOCUMENTS

| 5,164,310 | A | * | 11/1992 | Smith et al. | ............ 800/294 |
| 5,986,181 | A | * | 11/1999 | Trolinder et al. | ......... 800/314 |
| 5,994,624 | A | * | 11/1999 | Trolinder et al. | ......... 800/278 |
| 6,483,013 | B1 | * | 11/2002 | Reynaerts et al. | ......... 800/294 |

FOREIGN PATENT DOCUMENTS

WO   WO 97/43430   11/1997

OTHER PUBLICATIONS

Database WPI, Section Ch, Week 9723, Derwent Publications Ltd., London, GB; AN 97-252898, XP002103163 & JP 09 084477 A (Shikoku Coca-Cola Bottling KK), Mar. 31, 1997, See Abstract.
Database Cab, Cab International, Wallingford, Oxon GB 1998. Zhu Wieming: "Application of the Shoot Apical Meristem of Cotton in Gene Transformation by Particle Bombardment", XP002103162 & Jiangsu Journal of Agricultural Sciences, vol. 14, No. 2, pp. 74-79, See Abstract.

* cited by examiner

*Primary Examiner*—Medina A. Ibrahim
(74) *Attorney, Agent, or Firm*—Brown Raysman Millstein Felder & Steiner LLP

(57) ABSTRACT

This invention relates to methods for transforming cotton using isolated shoot apical tips of seedlings. The apical shoot tips of cotton seedlings are isolated and chilled at a low temperature to slow the metabolic activity of the isolated cells, and then inoculated with a transforming agent carrying a desired gene. The invention also provides a method of regenerating transformed cotton plants with a desired trait from transformed apical shoot tips.

5 Claims, No Drawings

METHODS FOR PRODUCING TRANSGENIC COTTON PLANTS USING CHILLED APICAL SHOOT TIPS

RELATED APPLICATIONS

This application is a continuation of application Ser. No. 09/252,477, filed on Feb. 18, 1999, now abandoned which claim priority under 35 U.S.C. §§ 119(e) and/or 365 to 60/075,261, filed in the United States on Feb. 19, 1998.

FIELD OF THE INVENTION

The present invention relates to a new method for the effective and reliable introduction of genes encoding desirable traits into the genome of a plant. The method includes the isolation and dissection of the apical meristematic region of the plant to be transformed, followed by introduction of DNA encoding the gene of interest at dissection site. The DNA is introduced under conditions which enhance the frequency of insertion of the foreign DNA encoding the desired gene of interest into the plant's genomic DNA.

BACKGROUND OF THE INVENTION

Current research in plant molecular biology is directed toward the development of improved plant varieties through the use of genetic engineering. Historically, improved plant varieties have been developed using classical genetic techniques to identify, preserve and crossbreed plants having desired traits. However, the genetic traits available to the classical breeder are limited to those that can be identified in the particular plant species the breeder is seeking to improve.

Advances in the application of the techniques of molecular biology to plants now allow for the introduction of new traits isolated from entirely different species into the plant of interest, particularly major crop plants such as cotton, maize, sorghum, soybeans, alfalfa, tobacco, and brassicas, such as rape. Traits that have been successfully transferred include insect resistance, herbicide resistance, stress tolerance, drought resistance, and disease resistance. Present day recombinant DNA technology has made it possible to identify new genes which effect the properties of plants and of products made from plants when they are transformed into new plant species. For example, a number of insect resistant varieties of cotton are presently being grown. Crop plants resistant to the herbicides Roundup®, Buctril®, and Liberty® Link are now available, as are tomatoes which can be left on the vine longer than normal tomatoes, making mechanical harvesting of tomatoes easier and cheaper.

A variety of techniques have been used to introduce foreign genes into plant cells. However, most of these techniques are limited to use with plant tissues that must be regenerated into whole plants and require a period of time in tissue culture. Methods of regenerating whole plants from cells or tissues include, micropropagation of apical and lateral meristems, organogenesis, and somatic embryogenesis. Transformation of apical meristems, lateral meristems and organogenesis produce chimeric plants, i.e., plants which have the gene encoding the newly introduced trait in only a few cells, which may or may not be in the gene in germline tissue. Plants regenerated through somatic embryogenesis are rarely chimeric. Somatic embryos are usually derived from a single cell.

One common method used to introduce foreign genes into plant cells is transformation with Agrobacterium, a relatively benign natural plant pathogen. Agrobacterium actively mediates transformation events—the integration of a gene providing a desired phenotypic trait—as part of the natural process it utilizes when it infects a plant cell. Methods for transferring foreign genes into plant cells and the subsequent expression of the inserted genes in plants regenerated from transformed cells are well known in the prior art. See for example, M. De Block et al., *The EMBO Journal* (1984) 3:1681; Horsch et al. *Science* (1985) 227: 1229; and C. L. Kado (*Crit. Rev: Plant. Sci.* (1991) 10:1.

Certain plant species have proved to be more difficult to transform with *Agrobacterium* than others, particularly members of the monocotyledonous plant family. Transformation of the dicot cotton has also been particularly difficult. Since monocotyledonous plants generally do not form crown galls, it was initially assumed that the host range of *Agrobacterium* was restricted to dicotyledonous plants. However, Stephen L. Goldman and Anne C. F. Graves described a process for transforming plants, including the monocot corn, in U.S. Pat. Nos. 5,177,010 and 5,187,073. These methods involve making a wound in a seedling in an area containing rapidly dividing cells, then inoculating the wound with *Agrobacterium*.

Roberta H. Smith and Jean H. Gould disclose a method for transforming plants via the shoot apex of a plant tissue in U.S. Pat. No. 5,164,310. These inventors teach that the method described permits rapid propagation of plants while perpetuating the unique clonal and genetic characteristics of the plant being transformed. But again, these methods have proved difficult to apply on a commercial scale due to the low numbers of transformants expressing a gene responsible for a desired trait that are actually produced.

Further improvements of methods for transforming plants by inoculating plant tissues containing rapidly dividing cells are disclosed in U.S. Pat. No. 5,169,770 issued to Paula P. Chee et al. Chee et al. demonstrate that the time after germination of infecting *P. vulgaris* seed with *Agrobacterium-based* vectors is critical to the ability of the *Agrobacteria* to infect meristematic cells. According to Chee et al., the amount of vascular tissue in germinating cells is rapidly increasing as differentiation proceeds. Therefore, the inoculation step must be conducted within 16 to 96 hours of germination to achieve successful transformation in this legume family of plants. Chee et al., further disclose that the transformation can be carried out with either an armed or disarmed *Agrobacterium* vector.

The technique known as microprojectile bombardment has been used to successfully introduce genes encoding new genetic traits into a number of crop plants, including cotton, maize, tobacco, sunflowers, soybeans and certain vegetables. See for example, U.S. Pat. No. 4,945,050, issued to Sanford; Sanford et al., *Trends in Biotechnology* (1988) 6:299; Sanford et al., *Part. Sci. Technol.* (1988) 5:27; J. J. Finer and M. D. McMullen, *Plant Cell Reports* (1990) 8:586–589; and Gordon-Kamm, *The Plant Cell* (1990) 2:603). Transformation by microprojectile bombardment is less species and genotype specific than transformation with *Agrobacterium*, but the frequencies of stable transformation events achieved following bombardment can be quite low, partly due to the absence of a natural mechanism for mediating the integration of a DNA molecule or gene responsible for a desired phenotypic trait into the genomic DNA of a plant. Particle gun transformation of cotton for example, has been reported to produce no more than one clonal transgenic plant per 100–500 meristems targeted for transformation. Only 0.1 to 1% of these transformants were capable of transmitting foreign DNA to progeny. See WO 92/15675. Cells treated by particle bombardment must be regenerated into whole plants, which requires labor intensive, sterile tissue culture procedures and is generally genotype dependent in most crop plants, particularly so in cotton. Similar low transformation frequencies have been reported for other plant species as well.

The methods of the prior art will provide transgenic plants in many types of plants. However, all of the presently available methods have been difficult to apply to the development of transgenic plant lives on a commercial scale due to the low numbers of transformants produced by the prior art transformation methods.

Thus, there still exists a need for procedures that will allow the delivery of a transforming agent, such as *Agrobacteria* carrying a foreign DNA encoding a desired trait, to germline tissues in a manner that provides efficient incorporation of the foreign DNA into the genomic DNA of the cells in these tissues. The method of the present application targets apical meristematic tissues in a manner that enhances incorporation of the foreign DNA into the genomic DNA of the plant greatly improving the frequency with which transformed plants can be produced.

SUMMARY OF THE INVENTION

The present invention provides a new method for transformation of cells of plant tissues and the regeneration of these cells and tissues into mature transgenic plants. Tissues containing the apical meristematic region of a plant seedling are isolated and treated to slow the metabolic activity of the tissue. This treatment provides a population of cells that accumulate in a single stage of mitosis. It also ensures that no new cell divisions occur. The tissue is then exposed to a transforming agent such as a DNA plasmid or an *Agrobacterium* carrying a plasmid vector which contains a DNA encoding a gene of interest. At an appropriate time, usually after about 24 hours the treatment is reversed, so that the metabolic activity of the tissue returns to normal, allowing the meristematic cells to enter mitosis synchronously and rapidly. Because the integration of a foreign DNA molecule encoding a desired trait of interest occurs most effectively during mitosis, the method of the present invention provides a larger population of receptive cells for exposure to transforming agents such as *Agrobacterium* carrying the gene of interest.

DETAILED DESCRIPTION OF THE INVENTION

The present invention relates to a method for producing transgenic plant cells and tissues, and to the mature plants produced therefrom. The method provides plant tissues which can effectively and efficiently integrate a gene of interest present on an *Agrobacterium* transformation vector or plasmid into its genomic DNA.

The method comprises the following steps:

1) isolation of apical shoot tips from young seedlings;

2) chilling of the isolated apical shoot tips for a sufficient period of time to slow the metabolic activity of cells and to accumulate the cells at a single stage of cell division or mitosis;

3) dissecting the shoot tip lengthwise through the cotyledon area while the shoot tip is maintained at the chilling temperature;

4) introducing a transforming agent carrying a foreign gene of interest into the dissected meristematic apical shoot tips; and 5) regenerating a plantlet from the transformed meristematic shoot tip on medium containing a selective agent.

The method of the present invention can be used to transform any species of plant, including monocots and dicots. The higher transformation frequencies achieved with the method overcome the difficulties associated with obtaining sufficient numbers of transformed plants to make screening feasible. Representative dicot plant species which may be transformed by the method of the present invention include cotton, soybeans, alfalfa, flax, tobacco, sunflowers, peanuts, fruits, such as strawberries and tomatoes, and vegetables such as peas, beans, squash, and peppers. Preferred dicots which can be used in the present invention include cotton, sunflower and pepper, particularly bell pepper. A preferred embodiment of the invention is the use of the method for transformation of a cotton plant. Monocot species which may be transformed using the method include maize, sorghum, barley, oats, rye, wheat, and rice.

The transforming agent used in the present invention can be a foreign gene selected to introduce or confer a desired trait into the transformed plant. It will be understood by those of skill in the art of plant molecular biology that the foreign gene will be comprised of DNA, or in certain instances may be comprised of RNA, such as antisense RNA. The trait to be introduced may promote growth of the plant, provide disease resistance, provide a change in plant morphology or in, quality of a plant product, or provide any other change which can be accomplished by genetic manipulation of the genome of the plant. DNA encoding the new trait to be inserted into the plant is generally in the form of a plasmid vector and is constructed using methodology known to those of skill in the art of plant molecular biology. Exemplary methods are described in *Current Protocols In Molecular Biology*, F. Ausubel et al. (eds.), Wiley Interscience (1990) and "Procedures for introducing foreign DNA into plants" in *Methods in Plant Molecular Biology and Biotechnology*, B. R. Glick, and J. E. Thompson, eds., CRC Press, Inc., Boca Raton, (1993).

The DNA to be expressed is flanked by a suitable promoter known to function in plant cells, such as the 35S promoter from cauliflower mosaic virus (CaMV), described by Odell et al., *Nature* (1985) 313:810; or the nopaline or octopine synthetase promoters (NOS) from *Agrobacterium*, described by Vontling et al., *Mol. Plant—Microbe Interactions* (1991) 4:370; and M. de Block et al., *The EMBO Journal* (1984) 3:1681. Any promoter which functions in a plant can be used to express the gene encoding the desired trait, including inducible, tissue-specific, tissue-preferred or constitutive promoters. Other regulatory sequences such as transcription termination sequences, polyadenylation sequences, and intervening sequences, or introns, which provide enhanced levels of expression may also be included in the DNA construct or plasmid used for transformation. Depending upon the desired function of the gene, it may be desirable to include protein sequences which direct the secretion or intracellular compartmentalizations of the DNA to be expressed. Such sequences are well-known to those of skill in the art of plant molecular biology.

The plasmid may also contain a DNA sequence encoding a selectable marker gene or a screenable marker gene, which can be used to identify individual transformed plants. The marker may allow transformed plants to be identified by negative selection or by screening for a product encoded by a genetic marker. Suitable selectable markers include antibiotic and herbicide resistance genes such as the neomycin transferase gene (NPTII) described by Fraley et al., *Proc. Natl. Acad. Sci. U.S.A.* (1983) 80:4803 and by van den Elzen et al., *Plant Mol. Biol.*, (1985) 5:299; the or the phosphinothricin acetyl transferase genes (Pat and bar) described in U.S. Pat. Nos. 5,561,236 and 5,276,268. Markers which may be used to directly screen for transformed plants include the β-glucuronidase gene (GUS), the luciferase gene, the green fluorescence protein gene and the chloramphenicol acetyltransferase gene. R. G. Jefferson, *Plant Molecular Biology Reporter* (1987) 5:387; C. Koncz et al., *Proc. Natl. Acad. Sci.* (1987) 84:131; Teri et al., *EMBO J.* (1989) 8:343; and De Block et al., *EMBO J.* (1984) 3: 1681. Any gene encoding a selectable or screenable marker known to function in plant cells or plant tissues may be used in the method.

Plants are transformed with genes encoded by DNA or by RNA which confers resistance to pathogens, disease or to pests, or with genes which alter and/or improve plant growth properties or the quality of plant products. For example, a gene encoding the *Bacillus thuringiensis* crystal endotoxin protein may be introduced into a plant to provide resistance to insects. Expression of this endotoxin in cells of a plant makes the plant tissues toxic when ingested by certain insect pests, providing transformed plants that are resistant to harmful insect pests. For a review of the known Bt endotoxin genes, see Kelly, et al., "Pesticide-Producing Bacteria," in *Mol. Biol. and Biotech.*, Meyers, ed, VCH Publishers, New-York, pp. 668 (1995). Genes encoding Bt endotoxins are also disclosed in K. F. Chak et al., *Applied and Environmental Microbiology* (1994) 60:2415; and R. S. Bora et al., *Applied and Environmental Microbiology* (1994) 60:214.

The gene to be transferred can provide herbicide resistance to the transformed plant. For example, expression of the bacterial gene enolpyruvylshikimate 3-phosphate synthetase in cells of the plant confers resistance to the herbicide glyphosate to the transformed plants. A mutant AroA gene, which can be used to confer tolerance to glyphosate, is described by Comai et al., in *Nature* (1985) 317:741–744. Insertion of the bar or pat genes isolated from strains of *Streptomyces* confers resistance to the herbicide glufosinate to the transformed plants. One preferred embodiment of the method includes transformation of a plant with the 2,4-D resistance trait encoded by the monooxygenase gene tfdA from *Alcaligenes eutrophus* as described in C. Bayley et al., *Theoretical and Applied Genetics* (1992) 83:645–649.

In one embodiment, the present invention may be used to transform plants with DNA molecules encoding fiber-specific genes such as those disclosed in U.S. Pat. No. 5,597,718. Such genes or their equivalents may be used to alter the fiber characteristics of the cotton plant. A preferred embodiment is the transformation of a cotton plant with a transforming agent comprised of DNA molecules encoding a fiber-specific gene. A gene which enhances the yield of the desired plant product may also be used to transform plants. Such yield enhancement genes are known to those of skill in the relevant art.

The desired genes are transformed into species of *Agrobacterium* which are then used for plant transformation. Convenient strains of *Agrobacterium* which are useful as vectors harbor a binary Ti plasmid system. These strains carry a first Ti plasmid having a virulence region and a second chimeric plasmid which contains the border regions of the T-DNA region of a wild-type Ti plasmid surrounding a chimeric gene construct which includes the foreign gene of interest. *Agrobacterium* strains which harbor cointegrate type Ti plasmids are also useful as vectors in the plant transformation methods of the present invention. Suitable binary and cointegrate Ti plasmids are well know to those of skill in the art of plant transformation. The binary system is preferred because the smaller plasmid, containing the T-DNA borders, can be constructed and manipulated in an alternative host such as *E. coli*, then reintroduced to *Agrobacterium*. Preferred species for use in the method of the present invention include *Agrobacterium tumefaciens* strains LB4404, EHA101, and EHA105.

Apical shoot tips of three day old seedlings are isolated and chilled to a temperature of about 2 to 8° C. to slow the metabolic activity of the tissues. This treatment results in the accumulation of the cells in the shoot tip in a single state of mitosis. This step can be carried out by storing the apical shoot tips of the seedlings in a laboratory refrigerator for a period of time sufficient for the cells to have completed at least one cell cycle and cell division. Storage at about 2 to 8° C. for approximately 24 hours is generally sufficient to synchronize the cells at a single point in the cell cycle. Under these conditions, any cell that has already begun to divide will continue through mitosis, but no additional cells will enter mitosis.

The shoot tips are removed from the refrigerator and maintained in cold water while the shoot tip is dissected lengthwise through the cotyledon area. Maintaining the low temperature during the dissection is needed to effectively reduce the amount of deleterious tissue exudate produced during the dissection. It is important to prevent the production of tissue exudate as much as possible to reduce damage tissue which will reduce the transformation frequency achieved. The shoot tip is split lengthwise through the cotyledonary axis to expose multiple germline sites to the transformation agent. The L2 germline layer that must be transformed in order to obtain transgenic progeny lies 6 cell layers below the epidermis, making it extremely difficult to reach in the intact shoot tip with any transformation agent, particle gun bombardment, *Agrobacterium*, electroporation, silicon carbide whiskers, vacuum infiltration, or sonication.

By splitting the shoot tip, a minimum of ten potential sites are directly exposed to the transformation agent. Methods have been devised for recovery of split meristems or shoot tips at a rate equal to that of intact meristems. Cells in the split meristems reorganize to provide new complete meristems. Additionally, methods have been devised for obtaining shoots from each of the ten target sites capable of reorganizing a complete meristem. The method of this application significantly increases the probability that a germline transformation event will occur by directly exposing the target sites to the transforming agent; increasing the number of target sites available; increasing the number of receptive cells in the target site, and decreasing the number and amount of inhibitory factors present in the tissue being transformed.

When the temperature of the dissected tissue is returned to normal, the meristematic cells enter mitosis synchronously and rapidly. Because the integration of the gene of interest most effectively occurs during mitosis, this procedure assures a larger population of receptive cells during exposure to the *Agrobacterium*.

After isolation, low temperature treatment, and dissection, the meristems are treated with nopaline, then inoculated with *Agrobacterium* containing the gene of interest that has been grown overnight in the presence of acetosyringinone. Shoot forming from the apical meristematic tissues are expected to be chimeric. Those forming from the basal cotyledonary area have a high probability of being non-chimeric.

The steps of the method disclosed in the present application increase the probability of obtaining germline transformants. The steps are central to the success of the efficient meristem transformation of cotton, or other species. They can be used not only with transformation methods which utilize recombinant *Agrobacterium,* they also increase the efficiency of transformation using all other transformation methods, including particle gun bombardment, electroporation, silicon carbide whiskers, vacuum infiltration and sonication.

EXAMPLE I

Apical shoot tips are isolated from three day old cotton seedlings, and chilled at about 2–8° C. in a refrigerator for 24 hours. Immediately following the chilling treatment, the apical shoot tips are dissected by cutting the tip lengthwise through the cotyledon area. The tips are maintained at about 2–8° C. during the dissection by placing them in a chilling water bath.

After they are dissected, the meristematic shoot tips are treated with nopaline at a concentration of 30 mM to support binding of the *Agrobacterium* used to introduce the gene encoding the desired trait of interest. The split meristematic tissues are then inoculated with the *Agrobacterium* which has been grown overnight in the presence of acetosyringinone. The split shoot tips are placed split side down on sterile filter paper moistened with Murashige & Skoog medium containing thisdurazon and co-cultivated with the *Agrobacterium* for 48 hours. The tissues are then transferred to fresh Murashige & Skoog medium containing glucose, kinetin, and napthalene acetic acid, which is supplemented with an appropriate antibiotic for eliminating the *Agrobacteria,* and with the appropriate selective agent. When they are transferred, the dissected tissues are placed upright with their basal ends immersed.

The meristematic tissues are transferred weekly to fresh selection medium. The root end of the tissue is trimmed to remove any transformed tissue at the base that might lead to the isolation of false positive shoots. New shoots are removed as they form and are placed singly on to fresh selective medium. When the first primary shoot is removed, buds at the base of the cotyledon then break, and form new shoots. As each new primary shoot forms, it is removed and placed directly onto selective medium. Removal of the primary shoot allows the buds to continue to break, providing a large population of new shoots. These shoots are followed, and those that are transformed are grown into mature plants. The shoot population produced following the transformation with *Agrobacterium* will consist of both chimeric and non-chimeric shoots. The shoots forming from the apical meristem will generally be chimeric, while those forming from the basal cotyledonary area will generally not be chimeric.

After six weekly transfers and base trimming, the shoots are transferred to rooting medium. After plants form at least 5 nodes, each leaf is spot tested with the selective agent. Positive plants are transferred to the greenhouse to await progeny analysis.

A method for producing a transformed plant which significantly increases the transformation efficiency of transformation by exposing transformation susceptible sites to the transforming agent in tissues which are at the same place in the cell division cycle has been described in detailed herein and illustrated by way of a specific example. Those of skill in the relevant art of plant molecular biology will understand that the invention as described may be modified in various ways and used with various materials, and that the descriptions of the embodiments disclosed herein are not intended to limit the invention to the particular methods and materials of those embodiments. The invention, as defined in the appended claims, covers all modifications, equivalents, and alternatives which fall within the spirit and scope of the disclosed methods and compositions.

References cited to supplement, explain, or provide details of methodology, techniques and compositions employed in the invention, and to provide a background for understanding the disclosed invention are hereby incorporated by reference.

We claim:

1. A method for producing a transformed cotton plant comprising,
    a) isolating apical shoot tips from three day old seedlings;
    b) chilling the isolated apical shoot tips at about 2°–8° Celsius for a time sufficient to slow cell division without damage to the cells, such that the cells become synchronized;
    c) dissecting the apical shoot tips to expose meristematic cells
    d) introducing a desired DNA molecule into the dissected apical shoot tips;
    e) placing the isolated apical shoot tips carrying the desired DNA molecule onto shoot development media at a temperature promoting cell division from the synchronized cells; and
    f) regenerating a transformed plant from shoot which form on the meristematic cells.

2. The method of claim 1, wherein the DNA molecule confers a desired phenotypic trait to the plant.

3. The method of claim 1, wherein the DNA molecule is introduced by *Agrobacterium* transformation.

4. The method of claim 1, wherein the DNA molecule is introduced by microprojectile bombardment.

5. The method of claim 1, wherein the apical shoot tips are chilled to about 2°–8° Celsius for about 24 hours.

* * * * *